United States Patent [19]

Farng et al.

[11] Patent Number: 5,019,284

[45] Date of Patent: May 28, 1991

[54] MULTIFUNCTIONAL LUBRICANT ADDITIVES AND COMPOSITIONS THEREOF

[75] Inventors: Lienpao Farng, Lawrenceville; Andrew G. Horodysky, Cherry Hill, both of N.J.

[73] Assignee: Mobil Oil Corporation, Fairfax, Va.

[21] Appl. No.: 381,882

[22] Filed: Jul. 19, 1989

[51] Int. Cl.$^5$ ................ C10M 137/04; C10M 135/18
[52] U.S. Cl. .................................. 252/46.7; 558/172
[58] Field of Search .............. 252/46.7, 32.7 E; 558/172

[56] References Cited

U.S. PATENT DOCUMENTS

| | | | |
|---|---|---|---|
| 2,998,347 | 8/1961 | Fancher | 558/172 |
| 3,008,977 | 11/1961 | Schrader | 558/172 |
| 3,018,216 | 1/1962 | Maxwell | 558/172 |
| 3,242,498 | 3/1966 | Stoffey | 558/172 |
| 3,259,540 | 7/1966 | Pianka | 558/172 |
| 3,317,426 | 5/1967 | Lowe | 252/46.7 |
| 3,980,574 | 9/1976 | Okorodudu | 252/49.9 |
| 4,104,181 | 8/1978 | Landis et al. | 252/46.7 |
| 4,333,841 | 6/1982 | Schmidt et al. | 252/46.7 |
| 4,544,492 | 10/1985 | Zinke et al. | 252/46.7 |
| 4,588,714 | 5/1986 | Haag et al. | 514/114 |
| 4,599,329 | 7/1986 | Seufert et al. | 514/119 |
| 4,770,801 | 9/1988 | Adams et al. | 252/46.7 |
| 4,938,884 | 7/1990 | Adams et al. | 252/46.7 |

Primary Examiner—Prince E. Willis
Assistant Examiner—Ellen McAvoy
Attorney, Agent, or Firm—Alexander J. McKillop; Charles J. Speciale; Howard M. Flournoy

[57] ABSTRACT

Ashless hydrogen phosphonate dihydrocarbyl dithiocarbamates have been found to be effective antioxidant/antiwear multifunctional additives for lubricants.

26 Claims, No Drawings

MULTIFUNCTIONAL LUBRICANT ADDITIVES AND COMPOSITIONS THEREOF

BACKGROUND OF THE INVENTION

This invention relates to multifunctional/antioxidant-/antiwear-EP additives and to compositions comprising lubricants, greases and other solid lubricants thereof containing a minor amount of an ashless organic hydrogen phosphonate derived from a dithiocarbamate.

The metal surfaces of machinery or engines operate under heavy or normal loads wherein the metal is under friction, even when being lubricated. Thus, there is always metal wear which in some cases can be excessive. It is clear that lubricants used to protect the metal surfaces do not completely prevent wear at the points of metal to metal contact. Consequently, the performance of the machine or engine will suffer, and in aggravated cases the machine or engine may be become completely inoperative from the wear caused by the friction and the load.

There have been many attempts to devise additive systems to improve the extreme pressure/load carrying properties of a lubricant. The non-metallic derivatives of the present invention provide lubricating oil compositions with enhanced antioxidant/antiwear and extreme pressure/load carrying characteristics and are believed to be capable of overcoming some of the aforementioned deficiencies of prior art additives.

Lubricants, such as lubricating oils and greases, are subject to oxidative deterioration at elevated temperatures or upon prolonged exposure to the elements. Such deterioration is evidenced, in many instances, by an increase in both acidity and viscosity, and when the deterioration is severe enough, it can cause metal parts to corrode. Additionally, severe oxidation leads to a loss of lubrication properties, and in especially severe cases this may cause complete breakdown of the device being lubricated. Many additives have been tried, however, many of them are only marginally effective except at high concentrations. Improved antioxidants are clearly needed.

Antioxidants or oxidation inhibitors are used to minimize the effects of oil deterioration that occur when, for example, hot oil is contacted with air. The degree and rate of oxidation will depend on temperature, air and oil flow rates and, of particular importance, on the presence of metals that may catalytically promote oxidation. Antioxidants generally function by prevention of chain peroxide reaction and/or metal catalyst deactivation. They prevent the formation of acid sludges, darkening of the oil and increases in viscosity due to the formation of polymeric materials.

Water (moisture) is another critical problem. In spite of even extraordinary precautionary efforts water is found as a film or in minute droplets in vessels containing various hydrocarbon distillates. This brings about ideal conditions for corrosion and damage of metal surfaces of the vessels and the materials contained therein. Also in the lubrication of internal combustion engines, for example, quantities of water are often present as a separate phase within the lubricating system. Another serious problem as previously mentioned in respect to metallic surfaces in contact with adjacent metallic surfaces is the surface wear caused by the contact of such surfaces. One material capable of simultaneously coping with such problems effectively is highly desirable.

The use of metal dithiocarbamates (such as zinc, nickel, or lead dialkyl dithiocarbamates) are known as effective antioxidants and antiozonants for many rubbers and polymers in various kinds of applications, such as styrene butadiene rubber and acrylonitrile butadiene rubber.

The use of non-metallic (ashless) dithiocarbamates, such as 4,4'-methylene bis(dibutyl dithiocarbamate), has been well known for their antioxidant and extreme pressure properties in lubricant applications.

The use of organic, dialkyl or diaryl hydrogen phosphonates, such as dibutyl hydrogen phosphonate and dioleyl hydrogen phosphonate, has been widely reported as having beneficial antiwear and extreme pressure properties.

It has now been found that the use of dithiocarbamate-derived organic hydrogen phosphonates provides exceptional antioxidant and antiwear/EP activity with potential high temperature stabilizing and metal passivating properties.

SUMMARY OF THE INVENTION

This application is directed to lubricant compositions containing small additive concentrations of N,N-dihydrocarbyl dithiocarbamate-derived hydrogen phosphonates which possess good antioxidant properties coupled with excellent antiwear and extreme pressure/load carrying activities. Both the dithiocarbamate moiety and the hydrogen phosphonate moiety are believed to provide the basis for the synergistic antiwear activity. The dithiocarbamate group is also believed to contribute significant antioxidant property to these novel additives.

All of these beneficial properties are believed to be enhanced as a result of this novel internal synergism. This unique internal synergism concept is believed to be applicable to similar structures containing (a) dithiocarbamate groups, and (b) hydrogen phosphonate groups within the same molecule. The products of this patent application show good stability and compatibility when used in the presence of other commonly used additives in lubricant compositions.

The lubricant compositions described herein are believed to be novel and their use as antioxidant/antiwear and extreme pressure/load carrying lubricant additives is also believed to be novel.

DESCRIPTION OF SPECIFIC EMBODIMENTS

Sodium dialkyl dithiocarbamates can be synthesized by reacting equal molar amounts of sodium hydroxide, a secondary dialkyl amine, and carbon disulfide in aqueous media or organic solution depending on conditions (Equation 1).

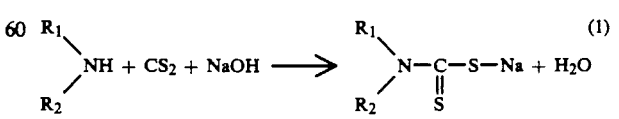

Similarly, triethylammonium salts of dithiocarbamates can be made by reacting triethylamine, dialkylamine and carbon disulfide in the non-aqueous media (Equation 2).

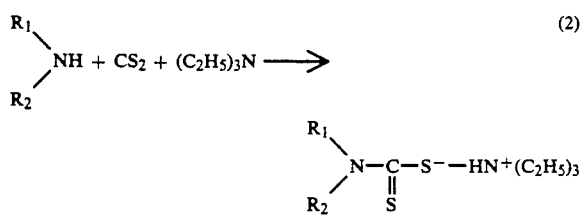

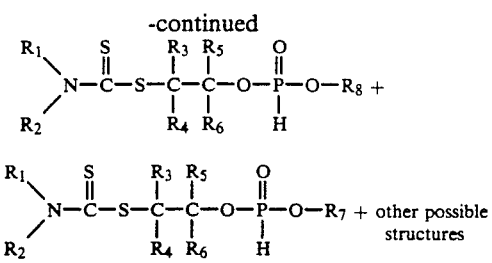

Alkylene oxides (epoxides) or epoxidized oils such as epoxidized soybean oil or related functionalized epoxides can be reacted with either sodium dihydrocarbyl dithiocarbamates or triethylammonium salts of dihydrocarbyl dithiocarbamates to form S-hydroxyalkyl N,N-dihydrocarbyl dithiocarbamates as generally described in Equation 3.

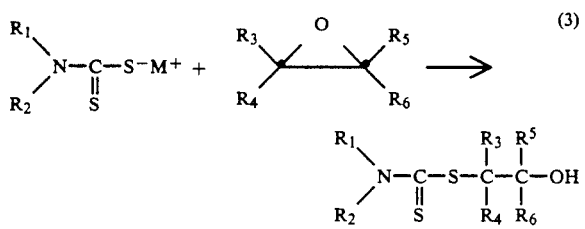

Where $R_1$, $R_2$, $R_3$, $R_4$, $R_5$, and $R_6$ are hydrogen, or $C_1$ to $C_{60}$ hydrocarbyl, and can optionally contain sulfur, nitrogen and/or oxygen.

$M^+$ represents the cationic moiety of dithiocarbamate salt, such as sodium ion ($Na^+$), triethylammonium ion [$(C_2H_5)_3N^+h$], or other suitable cations.

Alternatively, S-hydroxyalkyl dithiocarbamates may be prepared by the nucleophilic substitution of halohydrins with dihydrocarbyl dithiocarbamate salts as shown in Equation 4.

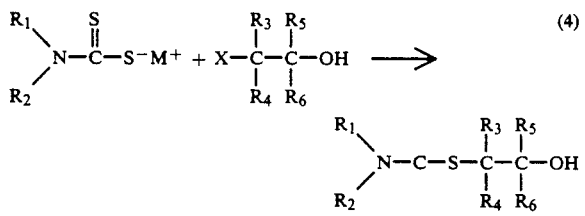

where X is halogen (Cl, Br, I).

The S-hydroxyalkyl N,N-dihydrocarbyl dithiocarbamates were further reacted with simple dialkyl hydrogen phosphonates (dialkyl phosphites) through transesterification to form the dithiocarbamate-derived hydrogen phosphonates as outlined below (Equation 5).

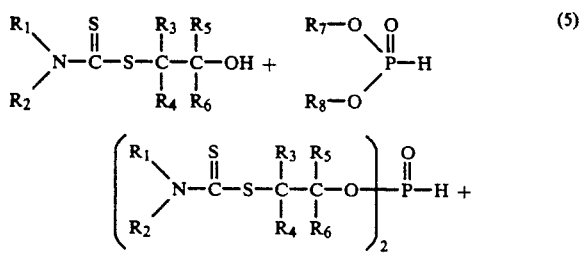

where $R_7$ and $R_8$ are $C_1$ to $C_6$ hydrocarbyl, preferably methyl, ethyl, propyl or butyl.

An excess of one reagent or another can be used. Molar quantities, less than molar quantities or more than molar quantities of epoxidizing agent or phosphite (hydrogen phosphonate) can be used.

The general reaction conditions may nevertheless be any suitable conditions known in the art. Temperatures will usually vary from about $-20°$ to about $250°$ C. If a solvent is used the temperature of reaction, etc. will vary accordingly. Usually atmospheric or ambient pressure is used, however, higher or lower pressures may be use if desired. The time of reaction will, or course, vary primarily with the temperature and pressure etc. used.

The base lubricants which are useful with the additives of this invention may be any oil of lubricating viscosity, whether natural, i.e., mineral, or synthetic or a mixture of mineral and synthetic oils.

The additives may therefore be incorporated into any suitable lubricating media which comprises oils of lubricating viscosity or greases in which the aforementioned oils are employed as a vehicle or into such functional fluids as hydraulic fluids, brake fluids, power transmission fluids and the like. In general, mineral oils and/or synthetic oils, employed as the lubricant oil, or grease vehicle may be of any suitable lubricating viscosity range, as for example, from about 45 SSU at 100° F. to about 6000 SSU at 100° F., and, preferably, from about 50 to about 250 SSU at 210° F. These oils may preferably have viscosity indices from about 70 to about 95. The average molecular weight of these oils may range from about 250 to about 800. Where the lubricant is to be employed in the form of a grease, the lubricating oil is generally employed in an amount sufficient to balance the total grease composition, after accounting for the desired quantity of the thickening agent and other additives components to be included in the grease formulation.

In instances where synthetic oil, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylolpropane esters, neopentyl and pentaerythritol esters, di(2-ethylhexyl) sebacate, di(2-ethylhexyl) adipate, dibutyl phthalate, fluorocarbons, silicate esters, silanes, esters of phosphorous-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis (p-phenoxy phenyl) ether, phenoxy phenylethers, etc.

Fully formulated lubricating oils may include a variety of additives (for their known purpose) such as dispersants, detergents, inhibitors, antiwear agents, antioxidant, antifoam, pour depressant and other additives including polyisobutyl succinimides, olefin copolymers, phenates, sulfonates and zinc dithiophosphates.

As hereinbefore indicated, the aforementioned additive compounds may be incorporated as multifunctional agents in grease compositions. When high temperature stability is not a requirement of the finished grease, mineral oils having a viscosity of at least 40 SSU at 150° F., and particularly those falling within the range from about 60 SSU to about 6,000 SSU at 100° F. may be employed. The lubricating vehicles of the improved greases of the present invention, containing the above described additives, are combined with a grease forming quantity of a thickening agent. For this purpose, a wide variety of materials are dispersed in the lubricating vehicle in grease-forming quantities in such degree as to impart to the resulting grease composition the desired consistency. Exemplary of the thickening agents that may be employed in the grease formulation are non-soap thickeners, such as surface-modified clays and silicas, aryl ureas, calcium complexes and similar materials. In general, grease thickeners may be employed which do not melt and dissolve when used at the required temperature within a particular environment; soap thickeners such as metallic (lithium or calcium) soaps including hydroxy stearate and/or stearate soaps can be used. However, in all other respects, any material which is normally employed for thickening or gelling hydrocarbon fluids or forming greases can be used in preparing the aforementioned improved greases in accordance with the present invention.

Included among the preferred thickening agents are those containing at least a portion of alkali metal, alkaline earth metal or amine soaps of hydroxyl-containing fatty acids, fatty glycerides and fatty esters having from 12 to about 30 carbon atoms per molecule. The metals are typified by sodium, lithium, calcium and barium. Preferred is lithium. Preferred members among thses acids and fatty materials are 12-hydroxystearic acid and glycerides containing 12-hydroxystearates, 14-hydroxystearic acid, 16-hydroxystearic acid and 6-hydroxystearic acid. Included among the other useful thickening agents are alkali and alkaline earth metal soaps of methyl-12-hydroxystearate, diesters of a $C_4$ to $C_{12}$ dicarboxylic acid and tall oil fatty acids. Other alkali or alkaline earth metal fatty acids containing from 12 to 30 carbon atoms and no free hydroxyl may be used. These included soaps of stearic and oleic acids.

Other thickening agents include salt and salt-soap complexes as calcium stearate-acetate (U.S. Pat. No. 2,197,263), barium stearate acetate (U.S. Pat. No. 2,564,561), calcium, stearate-caprylate-acetate complexes (U.S. Pat. No. 2,999,065), calcium caprylate-acetate (U.S. Pat. No. 2,999,066), and calcium salts and soaps of low-, intermediate- and high-molecular weight acids and of nut oil acids.

As has been disclosed hereinabove, the reaction products are useful as multifunctional antiwear/antioxidant/extreme pressure agents. They are added to the lubricating medium in amounts sufficient to impart such properties to the lubricant. More particularly, such properties will be imparted to the lubricant by adding from about 0.01% to about 10% by weight based on the weight of the total composition, and preferably from about 0.1% to about 3 wt %, of the neat product.

Having described the invention in general terms, the following specific examples are offered for purposes of illustration. No intention to limit the invention is to be inferred therefrom.

EXAMPLE 1

S-2-Hydroxypropyl N,N-Dibutyl Dithiocarbamate

Approximately 516 g of dibutylamine (4.0 mol) and 405 g of triethylamine (4.0 mol) were mixed in a three-liter, four-neck reactor equipped with thermometer, dropping funnel, Dean Stark trap condenser and agitator. Slowly 320 g of carbon disulfide (4.21 mol) was added dropwise to the reactor over a course of three hours at temperatures less than 35° C. Upon the completion of carbon disulfide addition, 235 g of propylene oxide (4.045 mol) was subsequently added over a course of two hours at ambient temperature ($\leq 30°$ C.). The resulting yellow liquid was further stirred at ambient temperature for two days. Thereafter, triethylamine was removed by vacuum distillation of 100° to 110° C. and this produced 1075 g of a viscous, reddish liquid as desired product.

EXAMPLE 2

Reaction Product of S-2-Hydroxypropyl N,N-Dibutyl Dithiocarbamate and Dimethyl Hydrogen Phosphonate Approximately 107 g of the above product of Example 1 (0.4 mol) and 22 g of dimethyl hydrogen phosphonate (dimethyl phosphite) were mixed in a 500 ml reaction flask. This mixture was heated at 75° C. for two hours, at 110° C. for four hours, and finally at 140° C. for one hour. Thereafter, all volatiles were removed by vacuum distillation to leave about 120.4 g of a viscous, orange fluid.

Product Evaluation

The products of Example 2 were blended into synthetic oils and evaluated by the Catalytic Oxidation Test at 325° F. for 40 hours (Table 1); and the Catalytic Oxidation Test at 325° F. for 72 hours (Table 2).

The Catalytic Oxidation test may be summarized as follows.

The test lubricant composition is subjected to a stream of air which is bubbled through the composition at a rate of 5 liters per hour. Present in the composition are metals commonly used as materials of engine construction, namely:

(a) 15.6 sq. in. of sand-blasted iron wire,
(b) 0.78 sq. in. of polished copper wire.
(c) 0.87 sq. in. of polished aluminum wire, and
(d) 0.167 sq. in. of polished lead surface.

Inhibitors for oil are rated on the basis of prevention of oil deterioration as measured by the increase in acid formation or neutralization number ($\Delta NN$) and kinematic viscosity ($\Delta KV$) occasioned by the oxidation.

TABLE 1

| | Catalytic Oxidation Test 40 Hours at 325° F. | | | |
|---|---|---|---|---|
| Item | Additive Conc. (wt %) | Percent Change In Viscosity $\Delta KV$ % | Change In Acid Number $\Delta TAN$ | Lead Loss, mg |
| Base Oil (200 seconds solvent refined, paraffinic neutral, mineral oil) | — | 57.9 | 4.78 | 2.9 |
| Example 2 | 1.0 | 17.1 | 3.47 | 0.0 |

TABLE 2

| Item | Catalytic Oxidation Test 72 Hours at 325° F. | | | |
| --- | --- | --- | --- | --- |
| | Additive Conc. (wt %) | Percent Change In Viscosity Δ KV % | Change In Acid Number ΔTAN | Lead Loss, mg |
| Base Oil (200 seconds solvent refined, paraffinic neutral, mineral oil) | — | 99.4 | 8.53 | 5.2 |
| Example 2 | 1.0 | 37.1 | 5.35 | 0.0 |

As shown above, the products of this invention show very good antioxidant activity as evidenced by control of increase in acidity, and viscosity.

The dithiocarbamate-derived hydrogen phosphonates were also evaluated for antiwear performance using the Four-Ball Test (Table 3).

The Four Ball Wear Test is, for example, previously disclosed in U.S. Pat. No. 3,423,316. In general, in this test three steel balls of SAE 52100 steel are held in a ball cup. A fourth ball positioned on a rotatable vertical axis is brought into contact with the three balls and is rotated against them. The force with which the fourth is held against the three stationary balls may be varied according to a desired load. The test lubricant is added to the ball cup and acts as a lubricant for the rotation. At the end of the test, the steel balls are investigated for wear scars; the extent of scarring represents the effectiveness of the lubricant as an antiwear agent. Results are also reported as wear rates in volume of wear per unit sliding distance per kilogram load. The lower the wear rate, the more effective the lubricant as an antiwear agent.

TABLE 3

| Item | Four Ball Test Wear Scar Diameter in MM (60 Kg Load, 30 Minute, 2000 rpm and 200° F.) |
| --- | --- |
| Base Oil (80% solvent paraffinic bright, 20% solvent paraffinic neutral minerals oils) | 4.44 |
| 1% Example 2 in above Base Oil | 0.75 |

The results of the wear test clearly show the good antiwear activity by dithiocarbamate derived phosphonates in accordance with the invention.

The use of additive concentrations of thiophosphates derived from dithiocarbamates in premium quality automotive and industrial lubricants will significantly enhance stability, reduce wear and extend service life. The novel compositions described in this patent application are useful at low concentrations and do not contain any potentially undesirable metals or cause corrosivity problems. These multifunctional additives can be commercially made using an economically favorable process which could be readily implemented.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. An improved lubricant composition comprising a major proportion of a oil of lubricating viscosity or grease or other solid lubricant prepared therefrom and a minor proportion of an ashless, non-metallic multifunctional antioxidant/antiwear/ extreme pressure additive product comprising a dithiocarbamate derived organic hydrogen phosphonate or mixtures thereof prepared by reacting in molar quantities, less than molar quantities or more than molar quantities a S-hydroxyalkyl N,N-dialkyl dithiocarbamate having the following generalized structure:

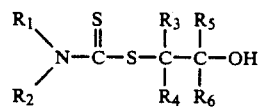

and a dihydrocarbyl hydrogen phosphonate having the following generalized structure:

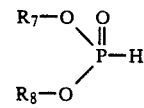

where $R_1$, $R_2$, $R_3$, $R_4$, $R_5$ and $R_6$ are hydrogen or $C_1$ to about $C_{60}$ hydrocarbyl optionally containing sulfur nitrogen and/or oxygen and where $R_7$ and $R_8$ are $C_1$ to about $C_6$ hydrocarbyl optionally containing nitrogen, sulfur and/or oxygen.

2. The composition of claim 1 wherein said additive product is a N,N-dialkyl dithiocarbamate-derived hydrogen phosphonate described by the following generalized structures:

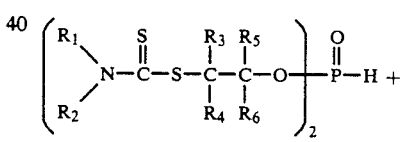

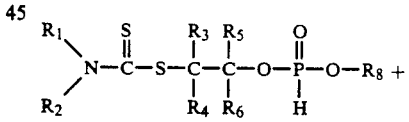

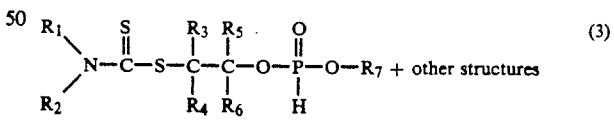

where $R_1$, $R_2$, $R_3$, $R_4$, $R_5$ and $R_6$ are hydrogen or $C_1$ to $C_{60}$ hydrocarbyl and optionally contain S, N and/or O, and $R_7$ and $R_8$ are $C_1$ to $C_6$ hydrocarbyl.

3. The composition of claim 2 wherein said additive product is as described by generalized formula (1).

4. The composition of claim 2 wherein said additive product is as described by generalized formula (2).

5. The composition of claim 2 wherein said additive product is as described by generalized formula (3).

6. The composition of claim 2 wherein said additive product is S-2-hydroxyhydrocarbyl N,N-dibutyl dithiocarbamate and a suitable hydrocarbyl hydrogen phosphonate.

7. The composition of claim 2 wherein said additive is the reaction product of S-2-hydroxypropyl N,N-dibutyl dithiocarbamate and dimethyl hydrogen phosphonate.

8. The lubricant compostion of claim 1 wherein the oil of libricating viscosity is selected from (1) mineral oils, (2) synthetic oils, (3) mixtures of mineral and synthetic oils or (4) greases prepared from (1), (2), or (3).

9. The lubricant composition of claim 8 wherein the oil is (1) a mineral oil.

10. The lubricant composition of claim 8 wherein the oil is (2) a synthetic oil.

11. The lubricant composition of claim 8 wherein the oil is (3) a mixture of mineral and synthetic oils.

12. The lubricant composition of claim 8 wherein said composition is a grease.

13. The composition of claim 8 containing from about 0.01 to about 10 wt % of said additive product.

14. The composition of claim 13 containing from about 0.1 wt % to about 3 wt % of said additive product.

15. An additive product of reaction comprising a mixture of dithiocarbamate derived organic hydrogen phosphonates prepared by reacting in molar quantities, less than molar quantities or more than molar quantities, a S-hydroxyalkyl N,N-dihydrocarbyl dithiocarbamate having the following generalized structure:

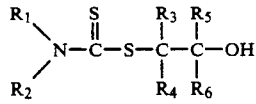

and a dihydrocarbyl hydrogen phosphonate having the following generalized structure:

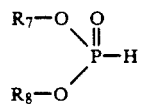

where $R_1$, $R_2$, $R_3$, $R_4$, $R_5$ and $R_6$ are hydrogen or $C_1$ to about $C_{60}$ hydrocarbyl optionally containing sulfur nitrogen and/or oxygen and
where $R_7$ and $R_8$ are $C_1$ to about $c_6$ hydrocarbyl optionally containing nitrogen, sulfur and/or oxygen.

16. The product of claim 14 containing at least one structure having the following generalized structure:

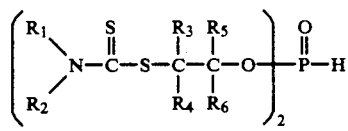

where $R_1$, $R_2$, $R_3$, $R_4$, $R_5$ and $R_6$ are hydrogen or $C_1$ to about $C_{60}$ hydrocarbyl optionally containing sulfur, nitrogen and/or oxygen.

17. The product of claim 15 containing at least one structure having the following generalized structure:

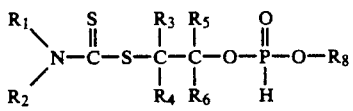

where $R_1$, $R_2$, $R_3$, $R_4$, $R_5$ and $R_6$ are hydrogen or $C_1$ to about $C_{60}$ hydrocarbyl optionally containing sulfur nitrogen and/or oxygen, and where $R_8$ is $C_1$ to about $C_6$ hydrocarbyl optionally containing nitrogen, sulfur and/or oxygen.

18. The product of claim 15 containing at least one structure having the following generalized structure:

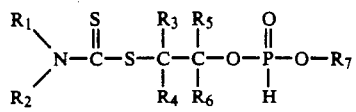

where $R_1$, $R_2$, $R_3$, $R_4$, $R_5$ and $R_6$ are hydrogen or $C_1$ to about $C_{60}$ hydrocarbyl optionally containing sulfur nitrogen and/or oxygen and where $R_7$ is $C_1$ to about $C_6$ hydrocarbyl optionally containing nitrogen, sulfur and/or oxygen.

19. The product of claim 15 wherein the reactants are S-2-hydroxypropyl N,N-dibutyl dithiocarbamate and dimethyl hydrogen phosphonate.

20. A compound having the following generalized structure:

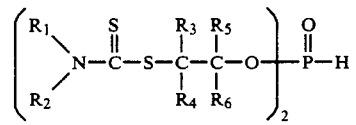

where $R_1$, $R_2$, $R_3$, $R_4$, $R_5$ and $R_6$ are hydrogen or $C_1$ to $C_{60}$ hydrocarbyl and can optionally contain S, N and/or O.

21. A compound having the following generalized structure:

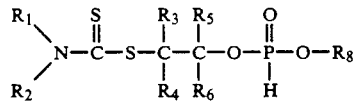

where $R_1$, $R_2$, $R_3$, $R_4$, $R_5$ and $R_6$ are hydrogen or $C_1$ to $C_{60}$ hydrocarbyl and can optionally contain S, N and/or O, and $R_8$ is $C_1$ to $C_6$ hydrocarbyl.

22. A compound having the following generalized structure:

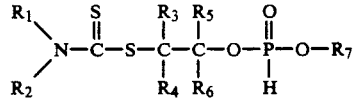

where $R_1$, $R_2$, $R_3$, $R_4$, $R_5$ and $R_6$ are hydrogen or $C_1$ to $C_{60}$ hydrocarbyl and can optionally contain S, N and/or O, and $R_7$ is $C_1$ to $C_6$ hydrocarbyl.

23. A method of making ashless dithiocarbamate derived organic hydrogen phosphonates comprising reacting in molar, less than molar or more than molar quantities a S-hydroxyalkyl N,N-dihydrocarbyl dithiocarbamate with a dihydrocarbyl hydrogen phosphonate at temperatures varying from $-20°$ to about $250°$ C., pressures varying from ambient to slightly higher for a time sufficient to obtain the desired product.

24. The process of claim 23 where the S-hydroxyalkyl N,N-dihydrocarbyl dithiocarbamate has the following generalized structure:

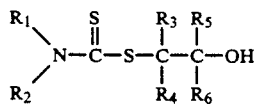

and where the dihydrocarbyl hydrogen phosphonate has the following generalized structure:

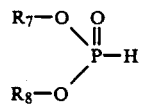

where $R_1$, $R_2$, $R_3$, $R_4$, $R_5$ and $R_6$ are hydrogen or $C_1$ to about $C_{60}$ hydrocarby optionally containing sulfur nitrogen and/or oxygen, and where $R_7$ and $R_8$ are $C_1$ to about $C_6$ hydrocarbyl optionally containing nitrogen, sulfur and/or oxygen.

25. The process of claim 24 where the reactant product is a mixture comprising material having at least one of the following generalized structures:

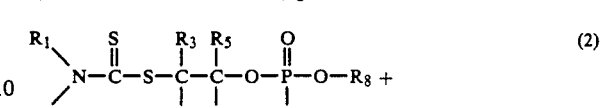

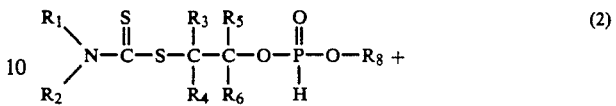

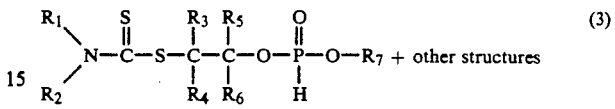

where $R_1$, $R_2$, $R_3$, $R_4$, $R_5$ and $R_6$ are hydrogen or $C_1$ to $C_{60}$ hydrocarbyl and can optionally contain S, N and/or O, and $R_7$ and $R_8$ are $C_1$ to $C_6$ hydrocarbyl and optionally contain S, N and/or O.

26. The process of claim 24 where the reactants are S-2-hydroxypropyl N,N-dimethyl dithiocarbamate and dimethyl hydrogen phosphonate.

* * * * *